United States Patent [19]

Lin

[11] Patent Number: 5,352,226
[45] Date of Patent: Oct. 4, 1994

[54] SIDE LOCKING SYSTEM ROTATABLE IN ALL DIRECTIONS FOR USE IN SPINAL SURGERY

[76] Inventor: Chih-I Lin, 513 S. Golden Pardos Dr., Diamond Bar, Calif. 10765

[21] Appl. No.: 14,525

[22] Filed: Feb. 8, 1993

[51] Int. Cl.⁵ .......................... A61F 5/00; A61B 17/56
[52] U.S. Cl. ................................................ 606/61
[58] Field of Search .............. 606/61, 60, 62, 69, 606/73, 59; 403/396, 90, 351

[56] References Cited

U.S. PATENT DOCUMENTS

| | | | |
|---|---|---|---|
| 683,513 | 10/1901 | Sprague | 403/90 |
| 4,827,918 | 5/1989 | Olerud | 606/61 |
| 4,946,458 | 8/1990 | Harms et al. | 606/61 |
| 5,030,220 | 7/1991 | Howland | 606/61 |
| 5,047,029 | 9/1991 | Aebi et al. | 606/61 |
| 5,053,034 | 10/1991 | Olerud | 606/61 |
| 5,176,680 | 1/1993 | Vignaud et al. | 606/60 |
| 5,224,396 | 7/1993 | Lobbezoo et al. | 403/90 |

Primary Examiner—Tamara Graysay
Attorney, Agent, or Firm—Bacon & Thomas

[57] ABSTRACT

A side locking system is rotatable in all directions for use in a spinal surgery. Such a system comprises a side locking member, a spherical liner, and a fastening element. The side locking member is composed of a side locking block and a rotatable locking block. The side locking block has a through hole for receiving and holding a spinal locking rod and has a fastening slit substantially perpendicular to the axis of the through hole. The rotatable locking block has a rotatable receiving mount of spherical construction. The spherical liner is mounted in the rotatable locking block and provided with a hollow portion so dimensioned as to receive and hold a spinal pin. The fastening element is capable of tightening the fastening slit of the side locking block so as to bring about a compression of the spherical liner, which in turn causes the through hole of the side locking block to clamp the spinal locking rod.

5 Claims, 2 Drawing Sheets

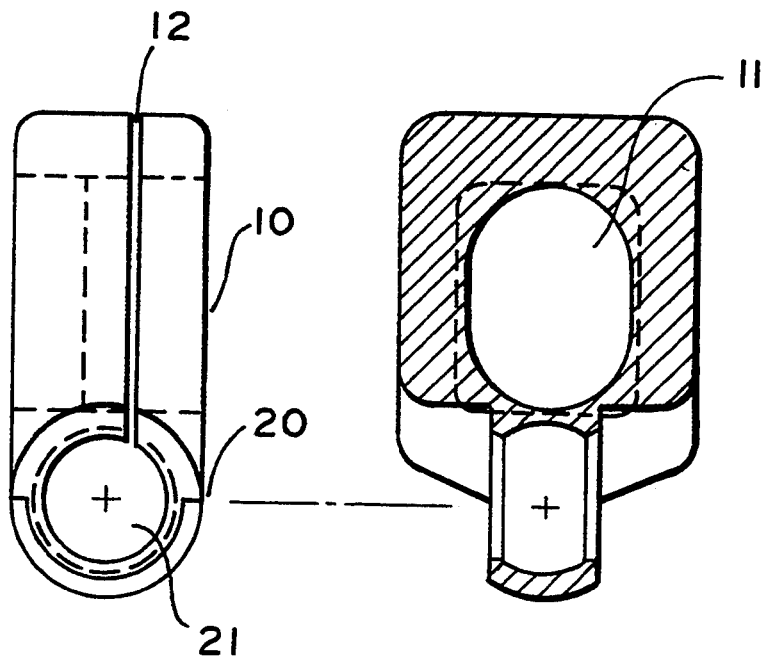
Fig. 1-a    Fig. 1-b
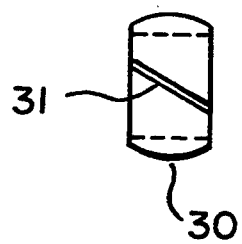
Fig. 2
Fig. 3
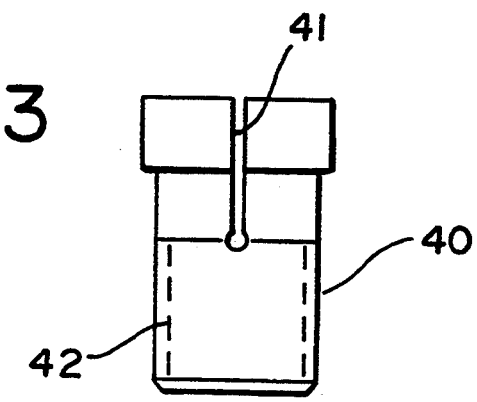

SIDE LOCKING SYSTEM ROTATABLE IN ALL DIRECTIONS FOR USE IN SPINAL SURGERY

FIELD OF THE INVENTION

The present invention relates to a spinal locking system, and more particularly to a side locking system which can be rotated in all directions so as to render an effective support to a vertebra under treatment.

BACKGROUND OF THE INVENTION

The implementation of a surgical implantation of the prior art vertebral locking and retrieving system requires that the spinal pins or the Lugue hooks which are inserted into vertebrae must be aligned. If a surgeon performing the surgical operation fails to attain such an alignment of the spinal pins or the Lugue hooks, he or she is forced to remedy the situation by bending the locking rod of the implanted system. Such a practice is not desirable because it often fails to bring about a satisfactory result of stabilizing the vertebrae under treatment.

With a view to overcoming the serious drawback of the prior art system described above, a variety of improved systems are disclosed in the U.S. Pat. Nos. 5,030,220; 4,827,918; 5,053,034; and 5,047,029. In addition to the above-identified patents, an improved system known as Diapason is disclosed by a French Company called Dimso. All these improved systems are by no means free from shortcomings. The improved system disclosed in the U.S. Pat. No. 5,030,220 is defective in design in that the clamp located at the curved portion of the locking rod can not be fastened effectively and that the clamp is capable of making only a unidirectional adjustment of the fastening angle of the spinal pins. The Diapason system has an advantage that it can be rotated in all directions; nevertheless it lacks an efficient locking effect in view of the fact that it is provided with the curved locking rod and that its spinal pins are ineffective when used at a location slightly far away from the locking rod. The systems of the U.S. Pat. Nos. 4,827,918; 5,047,029; and 5,053,034 are also limited in that they can be caused to make an angular adjustment of the spinal pins in only one direction, or in two directions at best, and that they are vulnerable to a mechanical failure due to their complicated structural make-up.

SUMMARY OF THE INVENTION

It is, therefore the primary objective of the present invention to provide a side locking system rotatable in all directions for use in a spinal surgery.

It is another objective of the present invention to provide a side locking system which can be rotated in all directions and has a spinal locking rod united securely with spinal pins.

It is still another objective of the present invention to provide a side locking system which can be rotated in all directions and is composed of a side locking member rotatable in all directions, a spherical liner and a fastening element.

In keeping with the principles of the present invention, the foregoing objectives of the present invention are accomplished by a side locking system which can be rotated in all directions and is composed of a side locking member, a spherical liner, and a fastening element.

The side locking member is made up of a side locking block and a rotatable locking block. The side locking block has a through hole intended for use in receiving therein a spinal locking rod and a fastening slit substantially perpendicular to the axis of the through hole. The rotatable locking block contains a rotatable receiving mount of a spherical construction.

The spherical liner is received in the rotatable locking block and provided with a hollow portion intended for use in receiving therein the spinal pin and the like. The spherical liner is further provided with a fastening slit.

The fastening element is used to fasten from the outside of the side locking block directly onto the fastening slit of the side locking block and indirectly onto the spherical liner, so as to cause the through hole of the side locking block to hold firmly the spinal locking rod.

The foregoing objectives, features, structures and functions of the present invention will be better understood by studying the following detailed description of a preferred embodiment of the present invention in conjunction with the drawings provided herewith.

BRIEF DESCRIPTION OF THE DRAWINGS

FIG. 1-a shows a top view of the preferred embodiment of the present invention.

FIG. 1-b shows a cross-sectional side view of the embodiment shown in FIG. 1-a.

FIG. 2 shows a schematic view of a spherical liner of the preferred embodiment of the present invention.

FIG. 3 shows a schematic view of a fastening element (without a fastening nut) of the preferred embodiment of the present invention.

DETAILED DESCRIPTION OF THE PREFERRED EMBODIMENT

Figure 4:
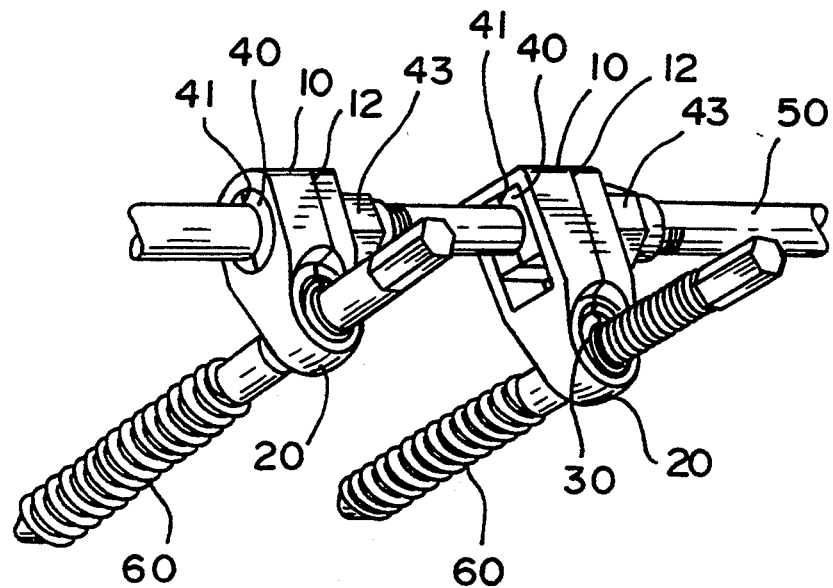
FIG. 4 shows a perspective view of the preferred embodiment in combination, according to the present invention.

Referring to all drawings provided herewith, the preferred embodiment of the present invention is shown to comprise a side locking block 10, a rotatable locking block 20, a spherical liner 30, and a fastening element 40.

The side locking block 10 has a through hole 11 intended for use in receiving and holding a spinal locking rod 50 and has a fastening slit 12 substantially perpendicular to the axis of the through hole 11. The rotatable locking block 20 contains therein a rotatable receiving mount 21 of a spherical construction.

The spherical liner 30 is mounted in the rotatable locking block 20 and provided with a fastening slit 31 and a hollow portion intended for use in receiving and holding a spinal pin 60.

The fastening element 40 has a slit 41, a threaded portion 42, and a nut 43. The fastening element 40 is used to fastened from the outside of the side locking block 10 directly onto the fastening slit 12 of the side locking block 10 and indirectly onto the spherical liner 30, so as to cause the through hole 11 of the side locking block 10 to hold firmly the spinal locking rod 50.

Figure 5:
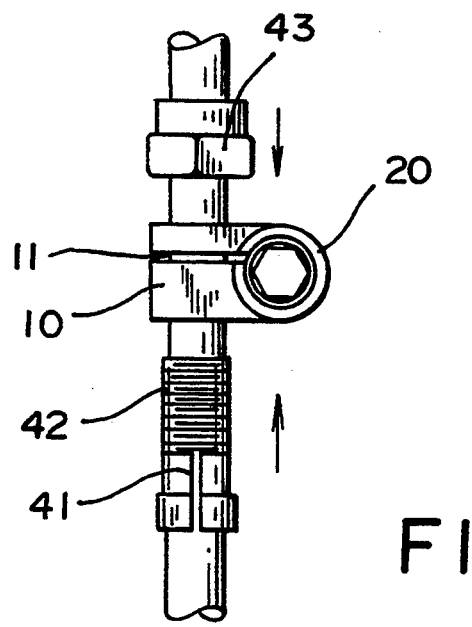
FIG. 5 shows a schematic view illustrating the fastening manner of the preferred embodiment of the present invention.

As illustrated in FIG. 4, two spinal pins 60 are inserted respectively into each of two vertebrae (not shown in the drawing) adjacent to a deformed vertebra (not shown in the drawing). A rigid connection between the two spinal pins 60 and the spinal locking rod 50 is attained by engaging the nut 43 with the threaded portion 42 in the directions indicated by arrows as shown in FIG. 5.

Before the side locking block 10 is tightened by the fastening element 40, the angle at which the spinal pin 60 is inserted into the vertebra can be adjusted at will, in view of the fact that the spherical liner 30 is mounted in the rotatable locking block 20 which can be rotated in all directions. As soon as the side locking block 10 is tightened by the fastening element 40, the fastening slit 12 of the side locking block 10 is forced to close, thereby causing the rotatable locking block 20 to clamp securely the spherical liner 30. As a result, the slit 31 of the spherical liner 30 is in turn forced to close so that the spherical liner 30 is caused to clamp securely the spinal pin 60, which is thus rigidly connected with the spinal locking rod 50, as shown in FIG. 4.

The component parts of the preferred embodiment of the present invention described above may be made of such biocompatible metal materials as a 316 LVM stainless steel, a Ti-6-4 material, an alloy of cobalt, molybdenum and chromium, etc.

The side locking block 10 of the present invention may be of any shape, preferably a rectangular shape or something similar to a rectangular shape. The through hole 11 located at the center of the side locking block 10 should be so shaped and dimensioned as to receive and hold the spinal locking rod 50. The through hole 11 of the side locking block 10 is preferably circular, or oval, or rectangular, or something similar to a rectangular shape in its cross section. It is suggested that the through hole 11 has an oval, or a rectangular cross section, which facilitates the adjustment of the position of the spinal locking rod 50 in the through hole 11. The fastening slit 12 of the side locking block 10 is substantially or nearly perpendicular to the axis of the through hole 11 or the axis of the spinal locking rod 50. The fastening slit 12 should be located on or near the major diameter of the through hole 11. If the through hole 11 is circular in its cross section, the fastening slit 12 is preferably located in such a manner that the fastening slit 12 is directed toward the center of the circular cross section of the through hole 11, and that the fastening slit 12 extends from one side of the side locking block 10 to reach the rotatable receiving mount 21 of the rotatable locking block 20. The fastening slit 12 may be also constructed in such a manner that it does not penetrate through the rotatable locking block 20.

The rotatable locking block 20 of the present invention may be of any shape. However, the rotatable receiving mount 21 of the rotatable locking block 20 is spherical in shape, with the exception of the openings located at both ends of the rotatable receiving mount 21. The spherical liner 30 is similarly constructed such that it has an outer diameter corresponding to an inner diameter of the rotatable receiving mount 21. The hollow portion of the spherical liner 30 is so shaped and dimensioned as to receive and hold the upper portion of the spinal pin 60. In general, the hollow portion of the spherical liner 30 is of a cylindrical construction. The slit 31 of the spherical liner 30 is so constructed that the slit 31 penetrates from the outer portion of the spherical liner 30 toward the inner portion of the spherical liner 30. The slit 31 is preferably oriented in an oblique manner relative to an axis defined by the hollow portion of spherical liner 30.

Any of the prior art fastening elements may be used as the fastening element 40 of the present invention, which serves the purpose of tightening the fastening slit 12 of the side locking block 10 so that the side locking block 10 is actuated to clamp securely the spinal locking rod 50, and that the rotatable receiving mount 21 of the rotatable locking block 20 is compressed to an extent that the spherical liner 30 is so tightened as to hold securely the spinal pin 60.

According to the present invention described above, the spinal pin 60 can be disposed in any desired orientation before it is inserted into a vertebra, in view of the fact that the rotatable receiving mount 21 of the rotatable locking block 20 can be rotated in all directions relative to the spinal locking pin 60.

The embodiment of the present invention described above is to be regarded in all respects as merely illustrative and not restrictive. Accordingly, the present invention may be embodied in other specific forms without deviating from the spirit thereof and is therefore to be limited only by the scope of the following appended claims.

What is claimed is:

1. A side locking system for use in spinal surgery comprising:
    a spinal locking rod;
    a side locking member including a side locking block and a rotatable locking block, said side locking block having a through hole receiving the spinal locking rod and having a fastening slit substantially perpendicular to an axis of said through hole that extends to said rotatable locking block, said rotatable locking block having a rotatable receiving mount of a spherical construction;
    a spinal pin adapted to be fastened within a vertebra;
    a spherical liner mounted in said rotatable locking block and provided with a hollow portion so dimensioned as to receive the spinal pin, said spherical liner further having a slit; and
    means for tightening said fastening slit of said side locking block so as to bring about a compression of said spherical liner in order to clamp said spinal pin, which in turn causes said through hole of said side locking block to clamp said spinal locking rod.

2. The side locking system according to claim 1 wherein said fastening slit of said side locking block is a through slit.

3. The side locking system according to claim 1 wherein said rotatable locking block and said spherical liner can be rotated, relative to each other, in all directions.

4. The side locking system according to claim 3 wherein said slit of said spherical liner is oriented obliquely with respect to an axis defined by said hollow portion.

5. The side locking system according to claim 1 wherein said slit of said spherical liner is oriented obliquely with respect to an axis defined by said hollow portion.

* * * * *